United States Patent
Srisathapat et al.

[19]

[11] Patent Number: 5,954,697
[45] Date of Patent: Sep. 21, 1999

[54] THREADED NUT SYRINGE PLUNGER FOR USE WITH A MEDICATION INFUSION PUMP

[76] Inventors: Chad Srisathapat, 8701 Vine Valley Dr., Sun Valley, Calif. 91352; Jeffery V. Funderburk, 17245 Lahey St., Granada Hills, Calif. 91344; Randy W. Adair, 27969 Skycrest Cir., Valencia, Calif. 91354

[21] Appl. No.: 09/033,328

[22] Filed: Mar. 2, 1998

[51] Int. Cl.⁶ ................................................. A61M 5/142
[52] U.S. Cl. ........................................... 604/155; 604/154
[58] Field of Search ................................... 604/155, 154, 604/152

[56] References Cited

U.S. PATENT DOCUMENTS

| | | |
|---|---|---|
| 2,498,672 | 2/1950 | Glass . |
| 3,858,581 | 1/1975 | Kamen . |
| 4,191,187 | 3/1980 | Wright . |
| 4,424,720 | 1/1984 | Bucchianeri .............................. 604/155 |
| 4,435,173 | 3/1984 | Siposs et al. ............................ 604/155 |
| 4,544,369 | 10/1985 | Shakoon et al. . |
| 4,562,751 | 1/1986 | Nason et al. . |
| 4,563,175 | 1/1986 | Lafond ..................................... 604/155 |
| 4,648,872 | 3/1987 | Kamen . |
| 4,678,408 | 7/1987 | Nason et al. . |
| 4,685,903 | 8/1987 | Cable et al. . |
| 4,719,825 | 1/1988 | Lahaye et al. ........................... 604/155 |
| 4,804,368 | 2/1989 | Skakoon et al. . |
| 4,838,857 | 6/1989 | Strowe et al. . |
| 4,976,696 | 12/1990 | Sanderson et al. . |
| 5,080,653 | 1/1992 | Voss et al. . |
| 5,097,122 | 3/1992 | Colman et al. . |
| 5,101,679 | 4/1992 | Smith et al. . |
| 5,176,502 | 1/1993 | Sanderson et al. . |
| 5,300,029 | 4/1994 | Denance ................................... 604/155 |
| 5,505,709 | 4/1996 | Funderburk et al. . |
| 5,520,653 | 5/1996 | Reilly et al. ............................. 604/152 |
| 5,681,286 | 10/1997 | Nichoff ................................... 604/155 |

FOREIGN PATENT DOCUMENTS

| | | | |
|---|---|---|---|
| 2495942 | 6/1982 | France ................................... 604/155 |
| WO9614893 | 5/1996 | WIPO . | |

*Primary Examiner*—Paul J. Hirsch
*Attorney, Agent, or Firm*—Mini Med Inc.

[57] ABSTRACT

An improved syringe is provided for use in a medication infusion pump for operating the syringe to administer a selected medication to a patient. The syringe comprises a hollow barrel adapted to receive a supply of the selected medication for delivery through infusion tubing or the like to the patient, in combination with a syringe plunger formed with an open-sided threaded half nut for engaging a motor-driven lead screw of the medication infusion pump when the syringe is correctly seated within a syringe compartment formed within a pump housing. The half nut on the syringe plunger includes detent tabs for snap-fit engagement with the pump lead screw to provide a direct drive connection therebetween. A compartment door on the pump housing can be moved to a closed position, following syringe placement into the syringe compartment, only when the plunger half nut is properly engaged with the lead screw.

17 Claims, 2 Drawing Sheets

THREADED NUT SYRINGE PLUNGER FOR USE WITH A MEDICATION INFUSION PUMP

BACKGROUND OF THE INVENTION

This invention relates generally to improvements in medication-containing syringes and related infusion pumps for controlled delivery of a selected medication from the syringe to a patient. More particularly, this invention relates to an improved syringe plunger adapted for direct drive connection with the infusion pump is a manner assuring proper interengagement between the syringe and pump.

Infusion pump devices and systems are relatively well known in the medical arts, for use in delivering or dispensing a prescribed medication such as insulin to a patient. In one form, such devices comprise a relatively compact housing adapted to receive and support a syringe carrying the prescribed medication for administration to the patient through infusion tubing and an associated catheter or the like. The infusion pump includes a small drive motor connected via a lead screw assembly for motor-driven advancement of a syringe piston plunger to deliver the medication to the patient. Programmable control means can be provided for operating the drive motor continuously or at periodic intervals to obtain a closely controlled and accurate delivery of medication over an extended period of time. Such infusion pumps are utilized to administer insulin and other medications, with exemplary pump constructions being shown and described in U.S. Pat. Nos. 4,562,751; 4,678,408; 4,685,903; 5,080,653; 5,097,122; and 5,505,709, which are incorporated by reference herein.

Infusion pumps of the general type described above have provided significant advantages and benefits with respect to accurate delivery of medication over an extended period of time. The infusion pump is often designed to be extremely compact and thus may be adapted to be carried by the patient, for example, by means of a belt clip of the like. As a result, important medication can be administered with precision and in an automated manner, without significant restriction on the patient's mobility or lifestyle.

To achieve accurate and reliable delivery of medication to the patient in response to motor-driven advancement of the syringe piston plunger, it can be extremely important to use a syringe designed to meet a narrow set of operational specifications which are compatible with the syringe pump. That is, variations in the size and shape of the syringe, friction forces attributable to sliding plunger seals, etc., can result in significant variations in the amount of medication delivered in response to operation of the pump drive motor. Moreover, the mechanical coupling between the pump lead screw and the syringe plunger, typically to include a lead screw nut and related latch mechanism for engaging a flange or the like on the syringe plunger, can inherently include a small degree of lost motion or backlash which can also result in significant variations in the medication delivery volumes. In addition, incorrect installation of the syringe into the infusion pump housing can cause inaccurate delivery or nondelivery of the medication to the patient.

In the past, modified medication infusion pumps and related syringes have been proposed with a direct drive connection between the syringe plunger and a pump lead screw, in attempts to provide medication delivery with improved precision. See, for example, U.S. Pat. No. 4,648, 872 and PCT WO 96/14893. In these proposals, the syringe plunger is equipped with a threaded element for engaging the pump lead screw, and a movable door or cover functions when closed to engage and hold the syringe in a position with the threaded element engaging the lead screw. While these designs provide the desired direct drive connection, they are dependent upon proper retention of the door or cover in the closed position to obtain proper medication delivery. If the door or cover becomes slightly ajar, the threaded element can become partially or completely disengaged from the lead screw, resulting in inaccurate partial delivery or nondelivery of the medication.

The present invention overcomes these problems and disadvantages by providing an improved syringe and related medication infusion pump, wherein the syringe plunger includes a threaded element adapted for secure direct drive coupling with a lead screw independent of the open or closed position of an infusion pump door or cover. However, in the event that the syringe plunger is not properly connected to the lead screw, an associated door or cover on the infusion pump cannot be closed thereby alerting the patient to such improper engagement.

SUMMARY OF THE INVENTION

In accordance with the invention, an improved medication-containing syringe and related infusion pump are provided for use in precision controlled delivery of a selected medication through infusion tubing or the like to a patient. The syringe includes a syringe plunger adapted for direct drive connection to a motor-driven lead screw of the infusion pump to achieve medication delivery with high precision. The syringe is shaped for mating fit into a syringe compartment formed by a housing of the infusion pump so that improper engagement or nonengagement of the syringe plunger with the lead screw will be indicated by an inability to close a compartment door.

The infusion pump comprises a compact pump housing having an elongated syringe compartment formed therein for receiving and supporting a medication-containing syringe barrel and associated piston plunger. A pump drive motor is operated in a programmable manner to dispense medication from the syringe. The drive motor includes a mechanical output such as a lead screw for controlled incremental rotation corresponding with predetermined medication doses to be dispensed from the syringe.

The syringe plunger comprises an elongated piston rod having a cylindrical nose end with appropriate seals slidably engaging the interior of the syringe barrel. The plunger rod projects rearwardly from the barrel and terminates in a radially projecting latch arm formed with an internally threaded half nut for direct drive engagement with the lead screw when the syringe barrel is seated within the syringe compartment. The half nut includes snap fit detent tabs for snap-fit engagement with the lead screw to releasibly retain the half nut in threaded direct drive connection with the lead screw. The size and shape of the latch arm and the half nut preclude closure of a hinged compartment door on the pump housing, unless the half nut is properly engaged with the lead screw.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 6:
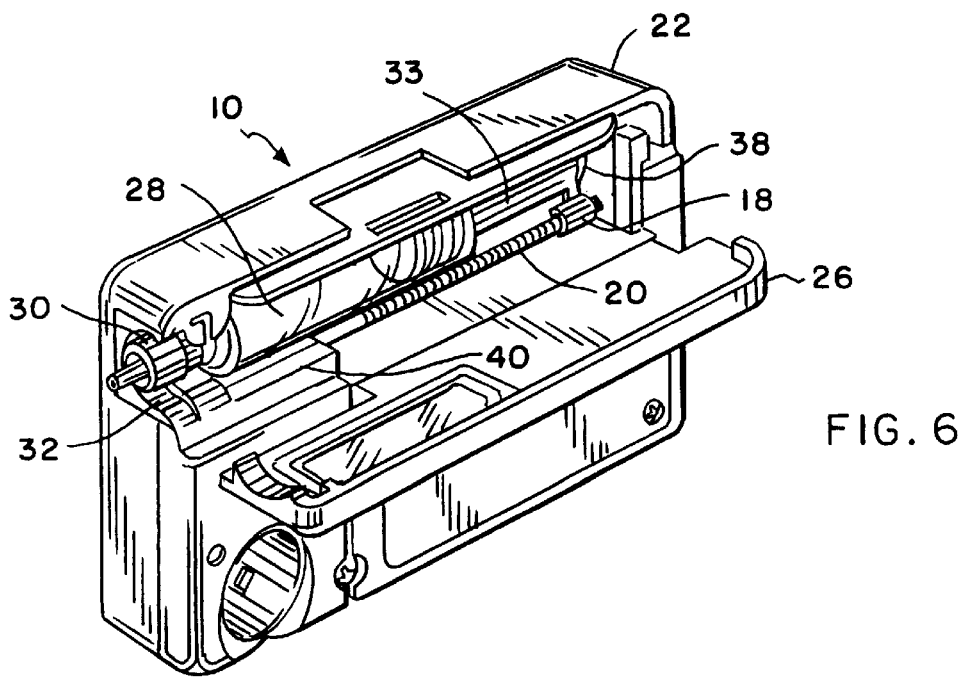
FIG. 6 is a rear perspective view similar to FIG. 3, and depicting proper placement of the syringe into the syringe compartment of the pump housing.

As shown in the exemplary drawings, a medication infusion pump referred to generally by the reference numeral 10 is provided for controlled administration of a selected medication to a patient. The infusion pump 10 is adapted to receive and support a medication-containing syringe 12 (FIGS. 3 and 6), and includes means for automatically and programmably operating the syringe 12 to deliver the medication through infusion tubing 14 (FIG. 3) or the like to the patient (not shown). In accordance with the invention, the syringe includes a syringe plunger 16 with a threaded half nut 18 formed thereon (FIGS. 36) for direct drive connection with a motor-driven lead screw 20 of the infusion pump 10. The direct drive connection is designed to assure positive and proper operation of the syringe, and further to insure that the syringe is fully and properly installed into the infusion pump.

Figure 2:
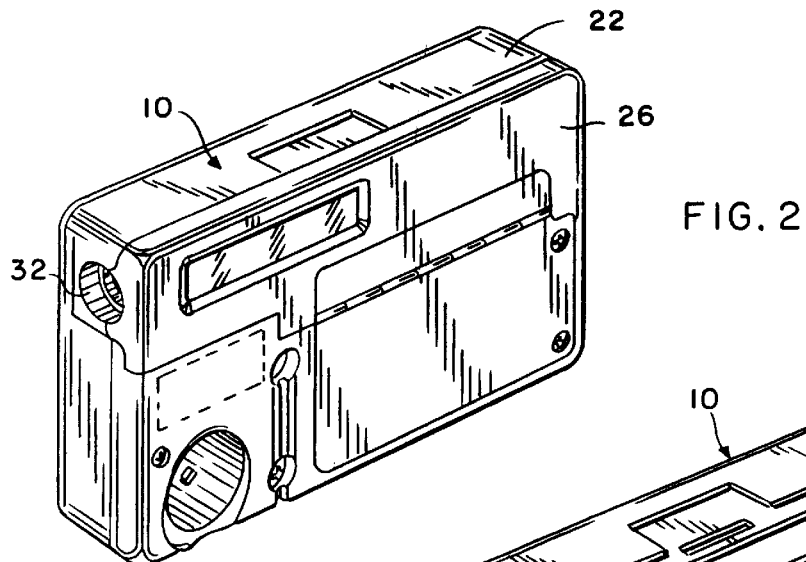
FIG. 2 is an enlarged rear perspective view of the infusion pump of FIG. 1.
Figure 3:
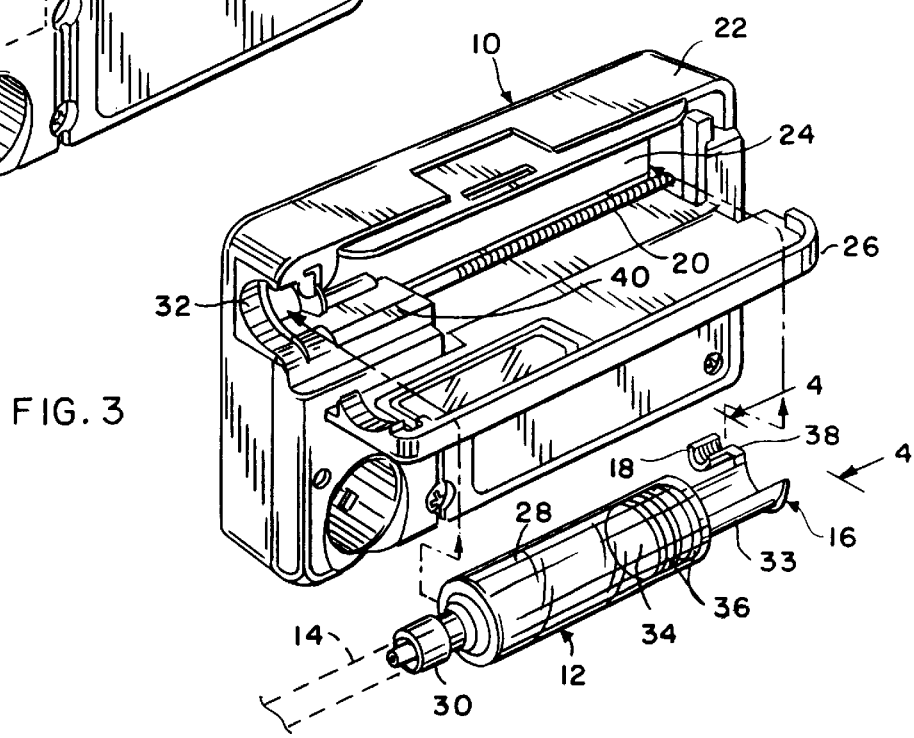
FIG. 3 is an exploded rear perspective view of the infusion pump of FIG. 2, illustrating a syringe compartment for receiving and supporting a medication-containing syringe, and wherein the pump and syringe are constructed according to the novel features of the invention.

The infusion pump 10 has an overall construction and operation which is generally known in the art. More specifically, with reference to FIGS. 1–3, the infusion pump 10 comprises a relatively compact pump housing 22 defining an elongated syringe compartment 24 (FIG. 3) adapted to receive and support the syringe charged with a selected medication, such as insulin, to be administered to the patient. FIG. 3 shows a hinged access door 26 in an open position at a rear side of the pump housing 22 to permit slide-fit or drop-in placement of the syringe 12 into the syringe compartment 24, after which the door 26 can be pivoted to a closed position (FIG. 2) during normal operation of the infusion pump. In general terms, the syringe 12 comprises a barrel 28 joined at a nose end thereof to a luer neck 30 having a size and shape for connection by means of an appropriate luer fitting (not shown) to the infusion tubing 14 shown in dotted lines in FIG. 3. As shown best in FIGS. 3 and 6, the luer neck 30 is adapted for seated reception within an outlet port 32 formed in the pump housing 22 whereby the infusion tubing 14 extends essentially from the outlet port 32 for delivery of the medication by means of a catheter (not shown) or the like to the patient.

The syringe plunger 16 extends from the rear or aft end of the syringe barrel 28, and may be advanced into the barrel to deliver the medication therefrom. In the preferred form as shown, the syringe plunger 16 comprises an elongated piston rod 33 having a generally semicircular cross-sectional shape terminating at a nose end thereof in a cylindrical plug 34 having one or more seal rings 36 thereon for slidably and sealingly engaging the interior of the syringe barrel 28. The piston rod 33 terminates at a rear end thereof in a laterally or radially projecting latch arm 38. The latch arm 38 in turn terminates in the internally threaded and open-sided half nut 18 of approximately semicircular cross section. The syringe plunger 16, including the piston rod 33 and the latch arm 38 with the half nut 18 thereon as described, is preferably constructed as an integral or one-piece plastic molding.

Figure 1:
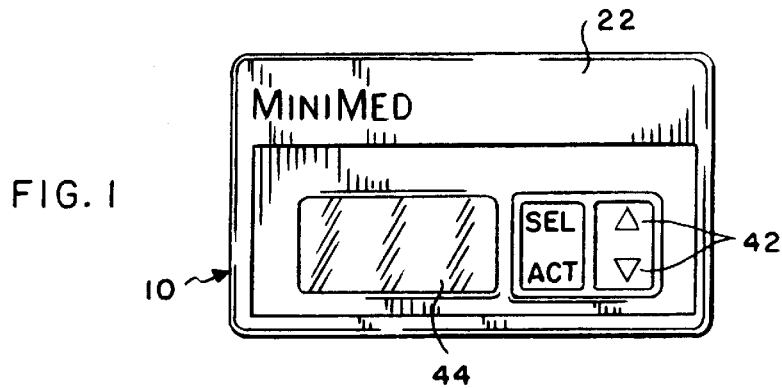
FIG. 1 is a front elevation view illustrating a medication infusion pump adapted for controlled delivery of a selected medication to a patient.

The threaded half nut 18 is sized and the threads are configured for mating engagement with the lead screw 20 shown within the pump housing 22 at one side of the syringe compartment 24 to extend generally in parallel with the syringe mounted within said compartment 24. The lead screw 20, during normal operation of the infusion pump, is rotatably driven by a drive motor shown generally by reference numeral 40 in FIGS. 3 and 6, to advance the plunger 16 within the syringe barrel 28 to dispense the medication in a precision controlled manner. The particular programmed operation of the pump can be set and revised by means of input keys 42 and a display 44 located at the front of the pump housing 22 (FIG. 1). Importantly, the half nut 18 and the latch arm 38 are rigidly linked to the piston rod 33 so that any and all mechanical lost motion or backlash is substantially eliminated, resulting in improved accuracy of medication delivery dosages.

Figure 4:
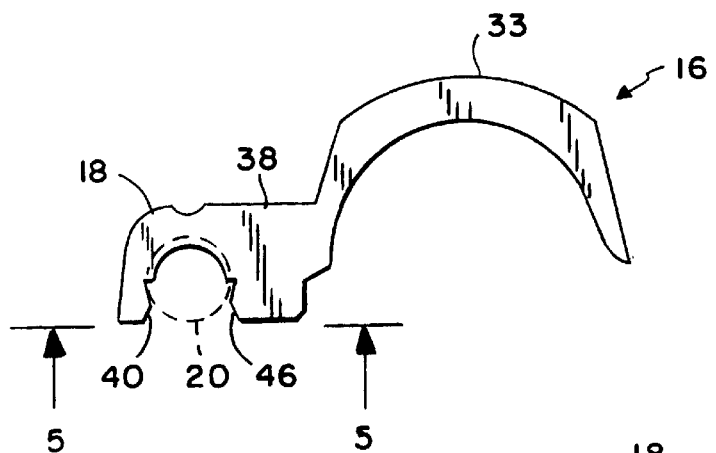
FIG. 4 is an enlarged end elevation view of a syringe plunger for the syringe, taken generally on the line 4—4 of FIG. 3.
Figure 5:
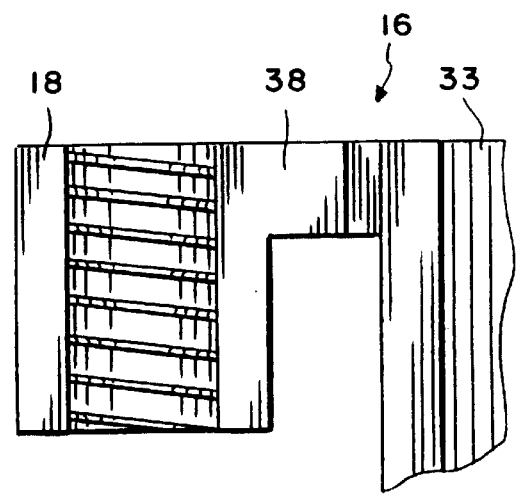
FIG. 5 is a further enlarged and fragmented view of a portion of the syringe plunger, taken generally on the line 5—5 of FIG. 4.

In accordance with a primary aspect of the invention, the threaded half nut 18 includes means for releasible snap fit engagement with the lead screw 20. More specifically, as shown in FIG. 4, the threaded segment of the half nut 18 extends through about 180 degrees for simple drop-in threaded engagement with the lead screw. The opposite ends of this threaded segment are each associated with a short inwardly extending detent tab 46, wherein these detent tabs 46 are disposed generally on a semicircular arc at positions greater than 180 degrees. With this geometry, drive engagement of the half nut 18 with the lead screw 20 requires the syringe 12 and/or the plunger 16 to be rotated within the syringe compartment 24 to place the half nut 18 over the lead screw, whereupon the half nut 18 can be pressed by a fingertip onto the lead screw with the desired snap fit engagement. In this engaged position, programmed rotation of the lead screw 20 advances the syringe plunger 16 for programmed delivery of the medication to the patient. Prior to operation, however, the compartment door 26 is desirably closed, with the latch arm 38 and associated half nut 18 obstructing such closure unless the half nut and lead screw are properly snap-fit engaged. When the syringe 12 reaches or nears an empty condition, the syringe can be removed quickly and easily for disposal by opening the door 26 and extracting the syringe from the compartment 24. Such syringe removal is accompanied by quick snap-like disengagement of the half nut 18 from the lead screw 20.

The present invention thus provides a mating direct drive connection between the motor-driven lead screw of the infusion pump 10 and the piston plunger 16 of the medication-containing syringe 12. The desired direct drive connection is achieved independent of the open or closed condition of a door 26 for the syringe compartment 24, yet an improper drive connection is indicated when normal closure of the door is obstructed. In addition, the semicircular or half round configuration of the piston rod 33 provides an open-sided chamber presented toward the bottom or base of the syringe compartment 24 when the syringe is installed therein, wherein this construction permits efficient use of the syringe compartment space for electronic or other components of the infusion pump and thereby enables improved space efficiency within the pump housing.

A variety of further modifications and improvements to the present invention will be apparent to those skilled in the art. Accordingly, no limitation on the invention in intended by way of the foregoing description and accompanying drawings, except as set forth in the appended claims.

What is claimed is:

1. In an infusion pump system including an infusion pump having a pump housing defining a syringe compartment for receiving and supporting a syringe, and an access door movable between open and closed positions, said syringe having a syringe barrel and a plunger received therein, said pump including a lead screw and means for controllably driving said lead screw, the improvement comprising:

an open-sided and internally threaded half nut carried by said plunger for threadably engaging said lead screw whereby rotation of said lead screw advances said plunger relative to said barrel to deliver medication from said syringe;

said half nut further including detent means for snap-fit engagement with said lead screw to retain said half nut in threaded engagement with said lead screw.

2. The combination of claim 1 wherein said half nut obstructs movement of said access door to said closed position unless said half nut is in snap-fit threaded engagement with said lead screw.

3. The combination of claim 1 wherein said open-sided half nut includes a threaded segment extending through an arc of about 180 degrees, said detent means comprising a pair of detent tabs projecting generally inwardly at opposite ends of said threaded segment.

4. The combination of claim 1 wherein said plunger comprises a piston rod slidably received into said syringe barrel and including a rear end projecting from said syringe barrel, and a laterally extending latch arm formed generally at said rear end of said piston rod, said half nut being formed on said latch arm.

5. The combination of claim 4 wherein said piston rod and said latch arm and said half nut are integrally formed from a molded plastic.

6. The combination of claim 4 wherein said piston rod has a generally semicircular cross sectional shape disposed to open toward a base of said syringe compartment when said syringe is received and supported therein.

7. An infusion pump system, comprising:

a syringe having a syringe barrel adapted to be filled with a selected medication, and a syringe plunger slidably received into said barrel and movable therein to deliver the medication therefrom;

said syringe plunger comprising an elongated piston rod having a rear end projecting from said barrel, and an open-sided and internally threaded half nut carried by said piston rod generally at said rear end thereof; and an infusion pump including a pump housing defining a syringe compartment for receiving and supporting said syringe, and drive means for engaging and controllably moving said plunger to deliver the medication from said syringe, said drive means including a rotatably driven lead screw;

said half nut including detent means for snap-fit engagement with said lead screw to retain said half nut in threaded engagement with said lead screw.

8. The system of claim 7 wherein said pump housing further includes an access door movable between an open position and a closed position for respectively opening and closing said syringe compartment, said half nut obstructing movement of said access door to said closed position unless said half nut is in snap-fit threaded engagement with said lead screw.

9. The combination of claim 7 wherein said open-sided half nut includes a threaded segment extending through an arc of about 180 degrees, said detent means comprising a pair of detent tabs projecting generally inwardly at opposite ends of said threaded segment.

10. The combination of claim 7 wherein said plunger further comprises a laterally extending latch arm formed generally at said rear end of said piston rod, said half nut being formed on said latch arm.

11. The combination of claim 10 wherein said piston rod and said latch arm and said half nut are integrally formed from a molded plastic.

12. The combination of claim 7 wherein said piston rod has a generally semicircular cross sectional shape disposed to open toward a base of said syringe compartment when said syringe is received and supported therein.

13. A syringe for use with a medication infusion pump having a rotatable lead screw for controllably dispensing medication from said syringe, said syringe comprising:

a hollow syringe barrel adapted for receiving and supporting a supply of a selected medication; and a syringe plunger slidably received into said barrel and movable therein to deliver the medication therefrom;

said syringe plunger comprising an elongated piston rod having a nose end slidably received within and sealingly engaging said barrel, said piston rod projecting from said nose end and terminating in a rear end disposed outside said barrel, said piston rod further including an open-sided and internally threaded half nut carried thereon generally at said rear end thereof, said half nut including detent means for snap-fit engagement with the lead screw of the infusion pump to releasibly retain said half nut in threaded engagement therewith.

14. The syringe of claim 13 wherein said open-sided half nut includes a threaded segment extending through an arc of about 180 degrees, said detent means comprising a pair of detent tabs projecting generally inwardly at opposite ends of said threaded segment.

15. The syringe of claim 13 wherein said plunger further comprises a laterally extending latch arm formed generally at said rear end of said piston rod, said half nut being formed on said latch arm.

16. The syringe of claim 15 wherein said piston rod and said latch arm and said half nut are integrally formed from a molded plastic.

17. The syringe of claim 13 wherein said piston rod has a generally semicircular cross sectional shape.

* * * * *